(12) United States Patent
Goebel Quintana (10) Patent No.: US 11,259,965 B2
(45) Date of Patent: Mar. 1, 2022

(54) COMBINED CORRECTIVE LENS AND LENS SHIELD

(71) Applicant: Alejandro A. Goebel Quintana, Houston, TX (US)

(72) Inventor: Alejandro A. Goebel Quintana, Houston, TX (US)

(*) Notice: Subject to any disclaimer, the term of this patent is extended or adjusted under 35 U.S.C. 154(b) by 429 days.

(21) Appl. No.: 16/306,868

(22) PCT Filed: Jun. 2, 2017

(86) PCT No.: PCT/US2017/035847
§ 371 (c)(1),
(2) Date: Dec. 3, 2018

(87) PCT Pub. No.: WO2017/210653
PCT Pub. Date: Dec. 7, 2017

(65) Prior Publication Data
US 2021/0041722 A1 Feb. 11, 2021

Related U.S. Application Data

(60) Provisional application No. 62/344,787, filed on Jun. 2, 2016.

(51) Int. Cl.
*A61F 9/02* (2006.01)
*B29D 11/00* (2006.01)
(Continued)

(52) U.S. Cl.
CPC ............... *A61F 9/02* (2013.01); *B29D 11/00* (2013.01); *B29D 11/00865* (2013.01);
(Continued)

(58) Field of Classification Search
CPC ....... A61F 9/02; A61F 2009/021; G02C 7/10; G02C 7/02; G02C 7/086; G02C 2202/16;
(Continued)

(56) References Cited

U.S. PATENT DOCUMENTS 5,152,788 A * 10/1992 Isaacson ............... A61F 2/1613
623/6.13
5,478,824 A * 12/1995 Burns .................. C08G 18/758
351/159.48
(Continued)

FOREIGN PATENT DOCUMENTS

SU 951219 A1 * 8/1982

OTHER PUBLICATIONS

Konovalov A.B. et al.—Svarnye soedineniya—Uchebnoe posobie, Sankt-Peterburg, 2010, p. 37, http://www.nizrp.narod.ru/svarnyesoed.pdf.*

*Primary Examiner* — Tuyen Tra
(74) *Attorney, Agent, or Firm* — Donn K. Harms (57) ABSTRACT

A combined corrective lens engaged with a lens shield and method therefor is provided. The lens shield is formed of a first lens portion which is subsequently engaged with an independently formed projecting portion. One surface of the projecting portion is configured for grinding to a prescription lens. The combined lens can include light filtering medium or layers only in the projecting portion or in both the projecting portion and first lens portion since the components are formed in advance and joined.

19 Claims, 9 Drawing Sheets

(51) Int. Cl.
    *G02C 7/08*           (2006.01)
    *G02C 7/02*           (2006.01)
    *G02C 7/10*           (2006.01)
    *G03B 21/14*         (2006.01)

(52) U.S. Cl.
    CPC .. B29D 11/00894 (2013.01); B29D 11/00932 (2013.01); G02C 7/02 (2013.01); G02C 7/086 (2013.01); G02C 7/10 (2013.01); G03B 21/14 (2013.01); *A61F 2009/021* (2013.01); *G02C 2202/16* (2013.01)

(58) Field of Classification Search
    CPC .... G02C 7/12; G03B 21/14; B29D 11/00865; B29D 11/00; B29D 11/00894; B29D 11/00932
    See application file for complete search history.

(56) References Cited

U.S. PATENT DOCUMENTS

| | | | | |
|---|---|---|---|---|
| 2012/0268712 A1* | 10/2012 | Egan | ............... | G02C 7/085 351/159.34 |
| 2014/0192313 A1* | 7/2014 | Riall | ............ | B29D 11/00817 351/158 |

* cited by examiner

COMBINED CORRECTIVE LENS AND LENS SHIELD

This application claims priority to U.S. Provisional Patent Application, Ser. No. 62/344,787, filed on Jun. 2, 2016, which is incorporated herein in its entirety by this reference thereto.

BACKGROUND OF THE INVENTION

1. Field of the Invention

The present invention relates generally to corrective lenses employed in eyewear such as eyeglasses, protective eyewear, and goggles. More particularly, the disclosed device and method relates to a formed eyewear lens having a first lens portion or shield formed of optical material and having one or a plurality of projections permanently positioned thereon, which are pre-configured or may be subsequently configured into corrective lenses.

2. Prior Art

Individuals with eyesight problems have turned to corrective eyewear for hundreds of years. As a general rule such eyesight problems are a result of the physical characteristics of the eye of the person requiring corrective lenses. Over the duration, such corrective lenses have been provided to users requiring them. The basic nature of grinding lenses to refocus the image captured by the eye of the user onto the receptive rear surface of their eye in a manner rendering clearer vision has progressed to provide corrections for issues other than near or far sightedness. However, the basic premise of positioning a lens in front of the eye of the user to refocus incoming light is still present today.

In some instances the nature of construction of corrective lenses has been less than adequate. For example, users of corrective lenses who suffer from severe farsightedness require very thick lenses to correct their vision. This requirement severely limits the eyeglass frames which can be employed for such users due to the perimeter thickness of conventionally formed lenses. Such a thick perimeter gives the eyewear a "bottle" look due to the thick sidewall.

Further, users with nearsightedness or farsightedness who or suffering from other vision acuity problems also have problems trying to wear sport goggles for activities such as skiing or motorcycling, as well as wearing safety goggles in hazardous environments. Conventionally, such users have been forced to try and fit their prescription eyeglasses within the cavity of the goggle or safety goggle covering their eyes and thereby must view their surroundings through both the goggle lens and their own lenses spaced between the goggle lens and their face. Such has led to poor vision from fogging and from shadow images, glare problems, and other issues caused by the interaction between their eyeglass lenses and the goggle lens or lenses they are positioned behind.

In prior art a partial solution to the problem has been advanced. For example U.S. Pat. No. 8,814,349 (Quintana) while a leap forward in the concept of providing a unitary structure of corrective lenses and panoramic or shielding lens, has shortcomings in the taught formation of the unitary structure. Quintana, while teaching the novel concept of using two projecting portions rising from one side of a first panoramic lens for formation of ophthalmic lenses, in practice has shown due to the taught construction, to be prone to cracking along perimeter of the projecting portions at their intersection with the front panoramic lens. Additionally, refraction of light through the sidewall of the projecting portions, at and adjacent their intersection with the front panoramic lens, may generate refractive qualities such as colorized light, which has been found to be distracting to users. Further, the taught construction in this prior art is the injection or other molding of a single lens component during molding, and therefore the projecting portions cannot be pre-configured as prescription lenses or have light filtering and films included.

The lens herein provides for one or a plurality of raised portions as corrective lenses which are formed prior to and separate from the first lens portion and which are joined thereto by ultrasonic welding, laser welding, adhesive, or other means to engage the perimeter edge of the raised portions, to a first surface of a thinner surrounding panoramic lens. Concurrently, the intersection of the perimeter of the projecting raised portions forming the ophthalmic lens is joined in a manner to prevent cracking and stress fractures over time. While not yielding a unitary structure of the two components due to an extremely small gap between the mating surface of the projecting portion and the first surface of the first lens portion, viewing aberrations through the gap which might occur over time from moisture and micronic dust therein, is prevented by a hermitic seal formed during the laser or sonic welding or by the adhesive layer therebetween.

By joining preformed projecting portions to formed first lens portions, the device herein is available for single lenses of eyewear as well as in dual lens configurations of protective eyewear shields and sport and protective goggle devices and in shapes which allow for formation of progressive lenses in both the horizontal and vertical direction The forgoing examples of related art and limitations related therewith are intended to be illustrative and not exclusive, and they do not imply any limitations on the invention described and claimed herein. Various limitations of the related prior art will become apparent to those skilled in the art upon a reading and understanding of the specification below and the accompanying drawings.

OBJECTS OF THE INVENTION

It is an object of this invention to provide a goggle or eyewear engageable lens having a first curved or panoramic lens which is permanently engaged with and surrounds one or a plurality of projecting portions connected thereon which may be precut to form ophthalmic lenses.

It is a further object of this invention to provide such a unitary structure where the first lens, or panoramic lens, on which the projecting portion extends, surrounds the projecting portion in a thinner cross section of optical material.

It is a further object of this invention to provide the projecting portions formed upon a surface of a surrounding larger curved panoramic lens, where the projecting portions may be pre-ground prior to joining the projecting portions to the first lens portion.

It is also an object of this invention to provide the projecting portions in shapes which may be precut to allow for progressive lenses in both the horizontal and vertical directions, which may then be joined to the surface of the first lens portion.

These and other objects, features, and advantages of the present lens invention and system herein, as well as the advantages thereof over existing prior art, which will become apparent from the description to follow, are accomplished by the improvements described in this specification and hereinafter described in the following detailed descrip-

SUMMARY OF THE INVENTION

The present invention is a lens formed into a joined structure featuring a first lens portion formed in a generally concave panoramic shape and having at least one projecting portion defined in shape by a perimeter edge thereof, rising from a permanent perimeter or adhesive connection with a first surface of the first lens portion. The cross sectional thickness of the first lens portion, surrounding the smaller area projecting portion, is thinner than the cross sectional thickness of the area within the bounds of the perimeter of the projecting portion rising from the first side of the first lens portion.

This first lens portion is formed of lens material which is optically correct, and in matching base curves on both sides, to yield a lens which is optically correct, across its entire surface. Once the projecting portion is joined at the perimeter with the first lens portion, the thinner surrounding area of the first lens portion is optically correct and significantly thinner in cross section to thereby allow engagement within a small or lightweight eyeglass frame or goggle, but still adapted for an engagement to temple portions to form a shield.

In all modes of the device herein, the intersection of the perimeter edge of the sidewall descending from a first side surface adapted for lens grinding, and which defines the shape of the projecting portion, forms such an intersection which is preferably neither a perpendicular nor an intersection of planar surfaces. Thus, at the intersection of the sidewall and the first surface of the first lens portion, radius or curved surface is formed. It is preferred that the radius of the curved surface be 0.1 mm to 0.4 mm to minimize the visual refractive and other defects of the final assembled lens, with 0.3 mm being particularly preferred. Such can be formed during sonic welding or laser welding or can be formed on the sidewall of the projecting portion which then is joined with adhesive to the first lens portion.

In all modes of the device herein, one or a plurality of such projecting portions, are preformed by molding, machining, or other means for preforming the projecting portions to a size and shape adapted for the prescription lens and user purpose. Such may be oval, square, curvilinear, serpentine, or any perimeter shape defining a shape of the projection desired.

In all modes of the device herein, the mating surface of the projecting portion or portions has the identical base curve as the first surface of the first lens portion to which it will be engaged. This yields a positioning of the mating surface which while not joined and unitary with the first surface of the first lens portion, is separated by a micronic gap therebetween. A subsequent perimeter welding by sonic welding or laser, or positioning of adhesive in the gap, will hermetically seal the gap or extremely small space between the mating surface of the projecting portions and the first surface of the first lens portion.

Recesses may be formed into the first surface of the first lens portion to aid in positioning. Such recesses in the shape of the perimeter of the projecting portions may be formed into the first surface of the panoramic lens to provide for registration of the projecting portions in positions upon the panoramic lens, prior to permanent engagement thereto.

For example, the spacing of the eyes of a user may be premeasured, and the shape of the appropriate projecting portions ground for lenses chosen. Thereafter, the first side of the projecting portions will be ground to form the correct prescription to correct the vision of that user. Thereafter, the recesses which can be preformed into the first surface of the first lens portion will provide a registration guide for the proper positioning of the projecting portions for that user. Once so positioned, the perimeter edge at the intersection of the sidewall of the projecting portions and the first surface of the first lens portion, may be welding with sonic or laser welding, or optionally an optically correct adhesive can be placed in the micronic gap between the mating surface and recessed first surface.

This system, by pre-forming the projecting portions, and engaging them to pre-formed and cured first lens portions, in a hermetic seal therebetween of the separate components, yields significant utility over a singularly formed unitary structure molded or formed of the two components. The unitary structure, formed as a unit in a mold, would still need to have the projecting portions ground in a special machine adapted for the very large panoramic first lens portion. Further, it does not allow for easy customization of the shape, and positioning of the projecting portions on the first lens portion which is customized to the users eye separation and facial structure.

The device and method herein, allows for choosing of the optimal shaped projecting portions and then pregrinding of the preformed projecting portions, to the correct prescription for the user. Further, the preformed projecting portions can be optimally positioned for the user's eyesight by premeasuring the optimal separation and positioning of the formed lenses of the projecting portions in front of the eyes of the user. Thereafter, the preformed and ground projecting portions, forming the corrective lenses, can be quickly joined to the first surface of the first lens portion in the registered positions determined by user measurements. This allows for the assembly of the device from components quickly and easily and a simple welding or adhesive to hermetically seal the micronic gap between the facing surface and first surface of the first lens portion.

Thus, the formed device and method herein, yield significant improvements in customization of the formed lens device not available in other preformed unitary structures where shapes, sizes, and positioning of the projecting portions cannot be customized, nor the lenses preground and then affixed.

Experimentation has shown a curve or arc formed at the communication of the lower end of the sidewall of the projections at an intersection with the first surface of the first lens portion, when adhered or sonically welded thereto, yields a perimeter sidewall intersection between the projecting portion and the first lens portion which resists cracking and fracturing under force or due to temperature changes the unitary lens encounters. Further, optical refractions and light flashes and the like have been found to diminish with this configuration over a linear intersection. This curve or arc may have a radius portion at the intersection of the sidewall around the perimeter edge of the projecting portion with the first surface of the first lens portion. This radius may be formed into the sonic welded portion after welding or into the abutting two surfaces after adhesion of the projecting portion to the surface of the panoramic surrounding first lens portion, or it may be formed into the perimeter edges of the projecting portions prior to affixing them to the first lens portion.

Other shapes of the intersection of the perimeter edge with the first lens surface which has shown to work well to prevent fractures is an inversed curve, a slanted portion at the intersection of a sidewall and first lens portion, as well as a radius or curved recess, however the radius or curve formed in the annular intersection of the sidewall defining the shape of the projecting portion, and the first surface of the first lens portion is a particular favorite. In some cases, the area formed by sonic welding may be formed in a manner to provide the structure to prevent cracking or deformation without the need for curves or another radius.

As noted, the projecting portion engagement to the first surface of the first lens portion may be accomplished by forming the projecting portion or portions in a first step, and then permanently engaging them adjacent each other by adhesive or perimeter edge welding. As noted, the lenses prescribed for the intended user can be preground before such engagement. As noted, a favored mode for such a permanent joining to form a unitary structure is by sonic welding around a formed ledge or around a perimeter of the projecting portion to form a connection with the first lens portion. Such avoids any issues related to temperature deformation and yields an excellent joining of the two surfaces of the projecting portion and first lens portion such that minimal or no distortion occurs in the view through the joined components.

Additionally, whether formed as a curved shield with a plurality of projecting portions thereon, or as a single lens for inclusion in eyeglass frames, by affixing the projecting portions which are preformed, not only can they be first ground to the prescription, a filtering medium or material can be included in the projecting portions which significantly reduces the cost if it does not have to be included in the large formed panoramic first lens portion.

Such a light filtering medium can be one or a combination of filtering mediums from a group including reflective film, a polarizing film or layer, an arc flash stopping layer, a photo chromatic layer or film, colorized optical material forming the projecting portion, or other light filtering medium.

Further, one or a combination of such filtering media can also be separately included in the first lens portion which can then be combined in a custom fashion with a chosen projecting portion to combine the effects of multiple light filtering media in the assembled device. By using such separate assembled components to form the device, the user can be provided with highly customized light filtering adapted to their vision shortcoming or their job or environment.

Still further, the shape of the projecting portion, the shape of which is defined by the sidewall intersecting the first surface of the first lens portion, can be formed in shapes as shown herein, or other shapes, which will allow for cutting of progressive lenses therein for the user. For example, one such shape, as shown in the figures, allows for portions of the projecting portion to extend closer to the bridge of the nose, while concurrently extending to the temple and well below the nose. This extended rectangular shape with a curve extending from a nose-side to the lower edge, allows for formation of progressive lenses which are highly customized to a user where the progressive lens can be both horizontal from top to bottom, and sideways from nose to temple. Since the surrounding section of the first lens portion is significantly thinner than the unitary portion of the projecting portion and first lens portion, the formed lens or shield can be configured for users.

Additionally shown herein, for lens grinding of an assembled lens device with un-ground projecting portions affixed to the first lens component, is a removable tooling engagement member which may be formed as part of the unitary lens. By formation of this tooling engagement member, in a break away or removable engagement extending perpendicular from the axis of the unitary lens and in a centered position, it allows for machining of the raised surfaces of the projecting portions to form corrective lenses, by an engagement of the unitary structure to a lens machining apparatus, using the removable projecting member.

As noted, tooling engagement, with the projecting member affixed to the curved panoramic first lens portion, is problematic, and the provided member overcomes the problems associated with the prior art, where the large curved panoramic first lens portion blocks engagement in a conventional fashion to lens grinding machines. Once the first surfaces of the projecting portions have been properly machined to the corrective lens, the projecting member can be removed by breaking a frangible portion or cutting it form the side edge.

Finally, the assembled lens herein is especially well adapted to the formation of protective eyewear, as well as for sport goggles and the like. In protective eyewear the noted sonic weld, laser weld, or adhesion and shaped intersection of projecting portion or portions at a respective perimeter to the first lens portion, alleviates the potential for the unitary lens cracking under impact or pressure as is a concern where that intersection is linear in nature as noted. Further, because a plurality of raised portions may be permanently engaged and extend from the first surface of the first lens portion surrounding the raised portions, and the first lens portion is large and panoramic and has thin edges, the assembled structure provides a goggle which is protected from fogging and the like.

In all modes both the first lens portion surrounding the engaged projecting portion, and the projecting portion or portions, may be formed of polycarbonate, glass, polymers such as allyl diglycol carbonate (ADC), trivex, and other injection molded material, such as a monomer plastic, or a "High Index" plastic. Sonic welding or laser welding will meld a formed ridge or portion of the perimeter of the projecting portion or portions with the surrounding first lens portion with minimal or insignificant impact on the refractive quality of the formed structure formed, to the eye of the user.

With respect to the above description, before explaining at least one preferred embodiment of the herein disclosed eyewear invention in detail, it is to be understood that the invention is not limited in its application to the details of construction and to the arrangement of the steps in the following description or illustrated in the drawings. The formed lens invention herein described is capable of other embodiments and of being practiced and carried out in various ways which will become obvious to those skilled in the art on reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing and carrying out the present disclosed system and eyewear apparatus. It is important, therefore, that the claims be regarded as including such equivalent construction and methodology insofar as they do not depart from the spirit and scope of the present invention.

Other aspects of the present invention shall be more readily understood when considered in conjunction with the above noted accompanying drawings, and the following detailed description, neither of which should be considered limiting.

DETAILED DESCRIPTION OF THE PREFERRED EMBODIMENTS

Figures 1, 2:
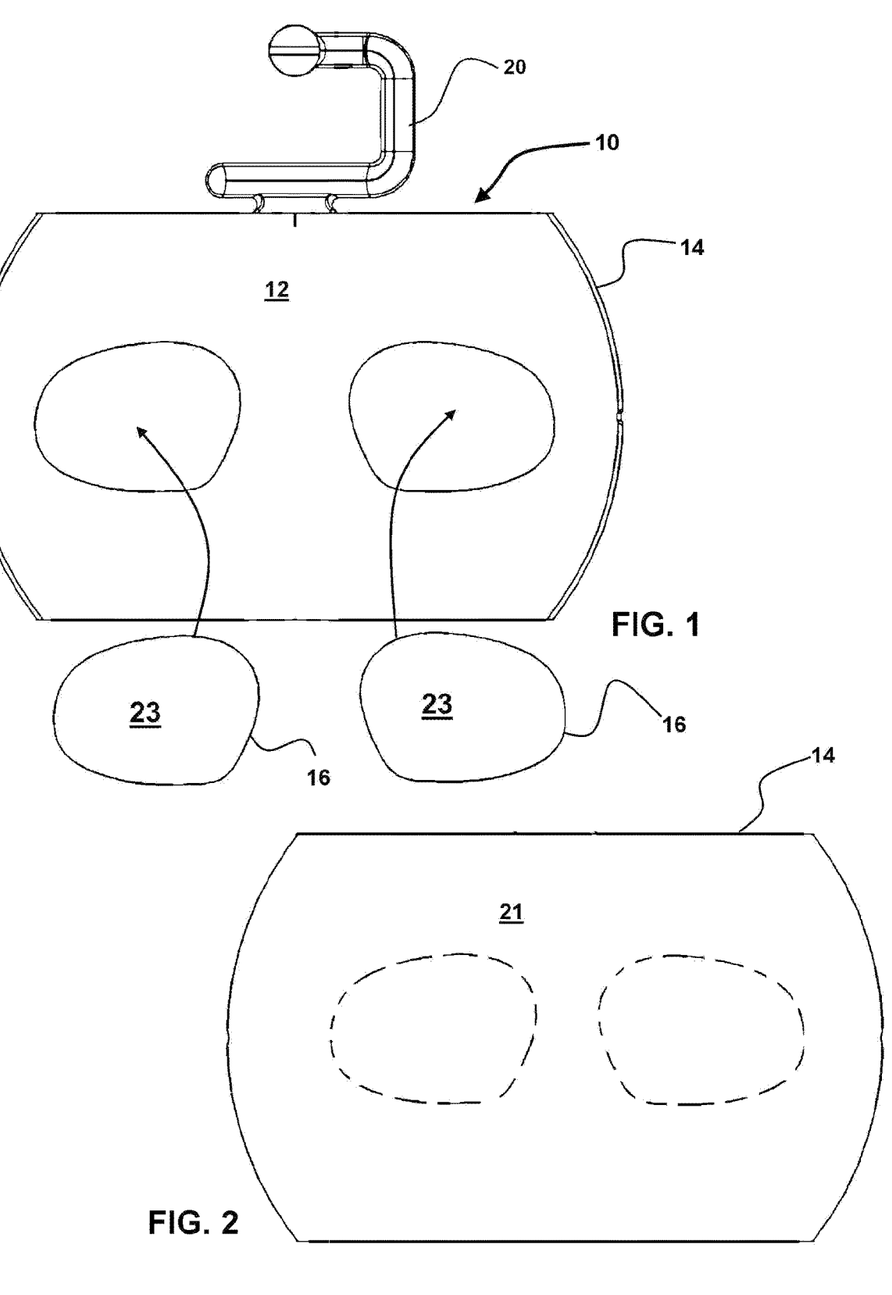
FIG. 1 depicts a view of the first surface of a first lens component of the assembled device, having a plurality of raised portions defined by a perimeter sidewall, engageable to permanent positions thereon to form a formed structure, which may be marked or recessed for proper registration with the eyes and face of a user in advance. Also shown is a removable tooling member.
FIG. 2 depicts a view of the opposite side of the first lens component from FIG. 1 showing the second surface and the shadowless appearance of the second surface provided by the formed structure of the projecting portion abutting the first surface of the first lens component.

Now referring to drawings of FIGS. 1-21, where similar structures are described with like numerals there is seen in FIG. 1 a view of the first surface 12 of a panoramic surrounding first lens component 14 configured for permanent connection adjacent a mating surface 15 of one or the shown plurality of raised or projecting portions 16. The shapes of the projecting portions 16 can vary to any perimeter shape which will serve the optical purpose intended, and are defined by a perimeter sidewall 17 which extends between a first side 23 adapted for grinding for prescription lenses to the mating surface 15.

In all modes of the device 10, the projecting portions 16 are formed separately from the first lens component 14, and have a mating surface 15 which has a base curve substantially identical to the curve of the first surface 12 of the first lens portion 14. While such forms a micro cavity between the two surfaces, the identical curves serve to eliminate refractive and aspheric issues in the assembled structure, once adhered or welded permanently.

As noted recesses 19 (FIG. 6) may be formed into the first surface 12 of the first lens portion 14 having a shape mirroring the perimeter shape of the portion portions 16. As noted such can be employed as a means for registration upon the first surface 12 of the first lens component 14, based on the measured user physical and eyesight characteristics, prior to affixing it using laser or sonic welding or adhesion thereto.

Also shown in figure extending from one side edge of the first lens portion 14 is shown a removable tooling member 21. It has been found in experimentation, that the tooling member 21 can be engaged with a grinding machine used to grind the individual first sides 23 of the projecting portions 16 to form the prescription or corrective lenses for a user. When the projecting portions 16 are not pre-ground prior to engagement to the first lens portion 14, this tooling member 21 is particularly preferred to ease lens formation.

FIG. 2 depicts a view of the opposite side or second surface 21 of the first lens portion 14 from that of the first surface 12 in FIG. 1. As depicted, the lens portion 14 with the engaged projecting portions 16 yields a formed structure of projecting portions 16 and first lens portion 14, with a shadowless appearance, viewed from the second surface 21.

Figure 3:
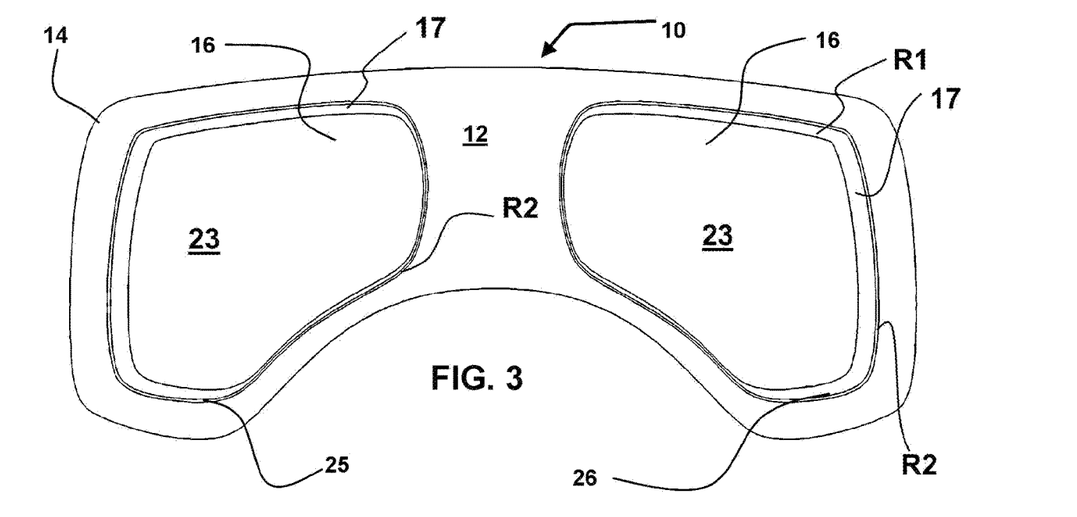
FIG. 3 depicts a view of a panoramic first lens portion having projecting portions permanently engaged with sonic or laser welding or adhesive or the like, and having a shape defined by a perimeter sidewall extending to an intersection with the first surface of the first lens component.

FIG. 3 depicts a view of the first surface 12 of the panoramic first lens portion 14, having projecting portions 16 permanently engaged to the first surface 12. The intersection 25 of the sidewall 17 of the projecting portion 16 and the first surface 12 is as noted curved or has a radius. The projecting portion 16 can be joined to the first surface 12 of the first lens portion 12 using sonic welding, laser welding, adhesive, or other connections as may occur to those skilled in the art which hill hold the mating surface 15 of the projecting portions 16 adjacent to the first surface 12 of the first lens portion 14. Also shown is the curvilineal shape of the projecting portions 16 as defined by the sidewall 17 thereof.

Figure 4:
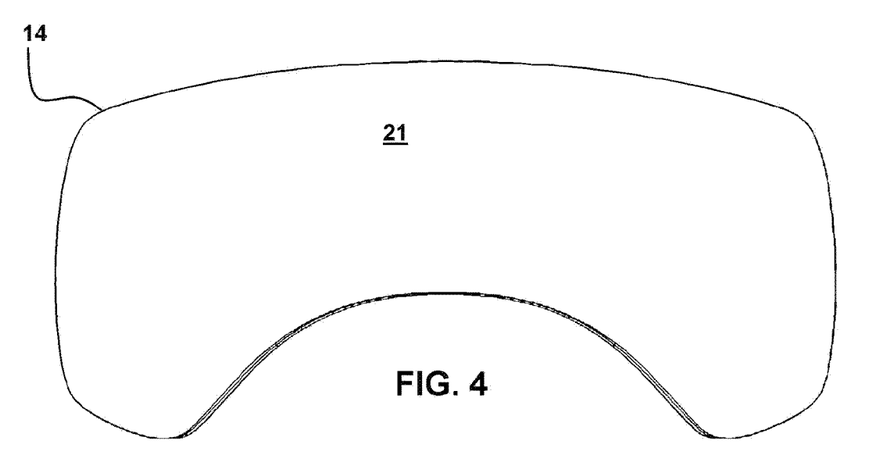
FIG. 4 is a front view of the first lens portions of FIG. 3.

FIG. 4 is a front view of the second surface 21 of the panoramic sized first lens portion 14 of FIG. 3 which surrounds the perimeter edges of both projecting portions 16.

Figure 5:
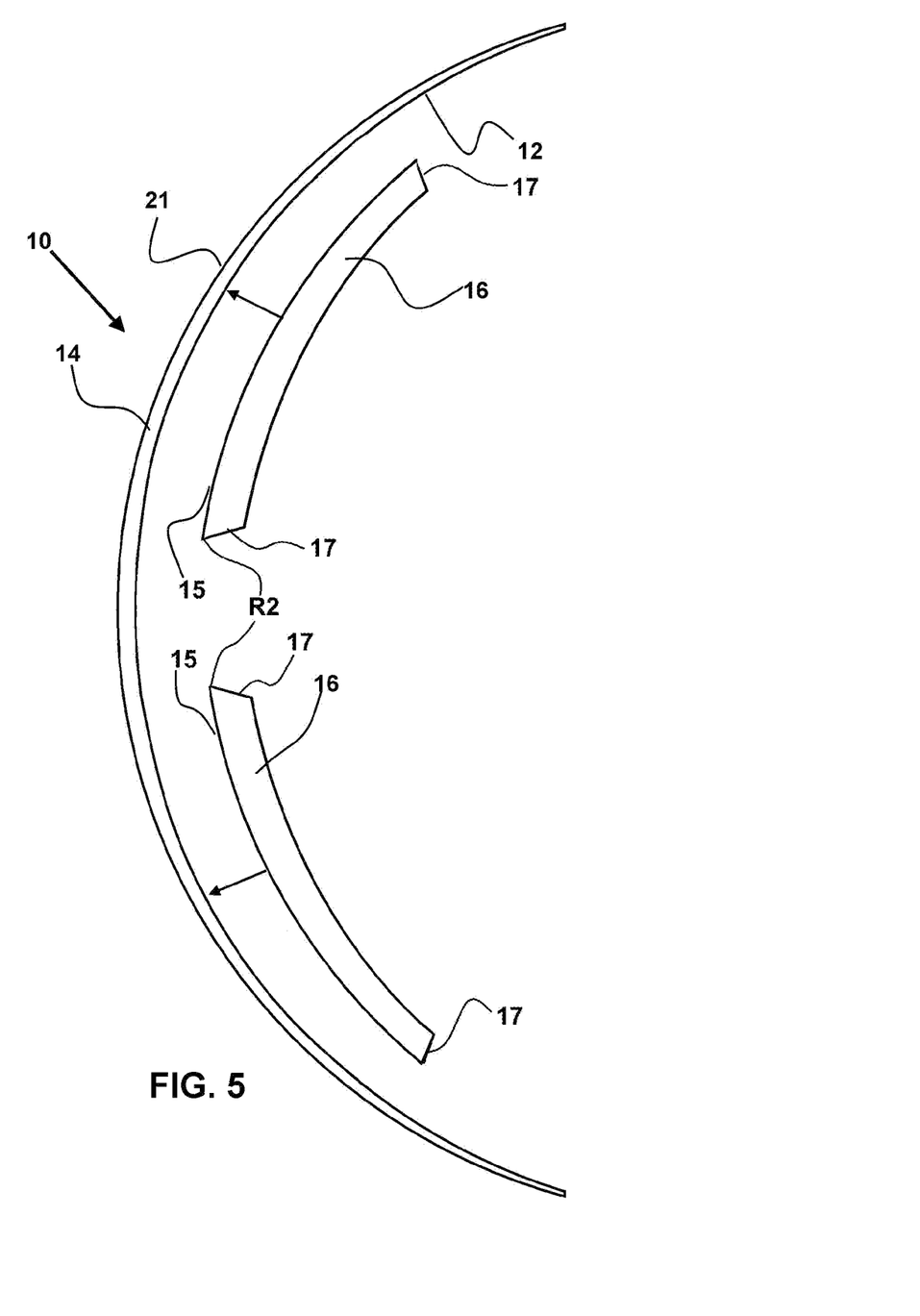
FIG. 5 depicts a side view of two projecting portions which are positionable against the curved surface of the first lens portion for sonic welding or adhesion thereto to form a formed structure of projecting portions and surrounding first lens portion.

FIG. 5 depicts a side view of two projecting portions 16 which have been pre formed and configured with a mating surface 15 having a base curve mirroring that of the first surface 12 to mate adjacent the curved first surface 12 of the first lens portion 14. Both projecting portions 16 will be permanently engaged thereto, using sonic welding, laser welding, adhesion, or other means of engagement as would occur to those skilled in the art, to form a structure of projecting portions 16 and surrounding first lens portion 14.

Figure 6:
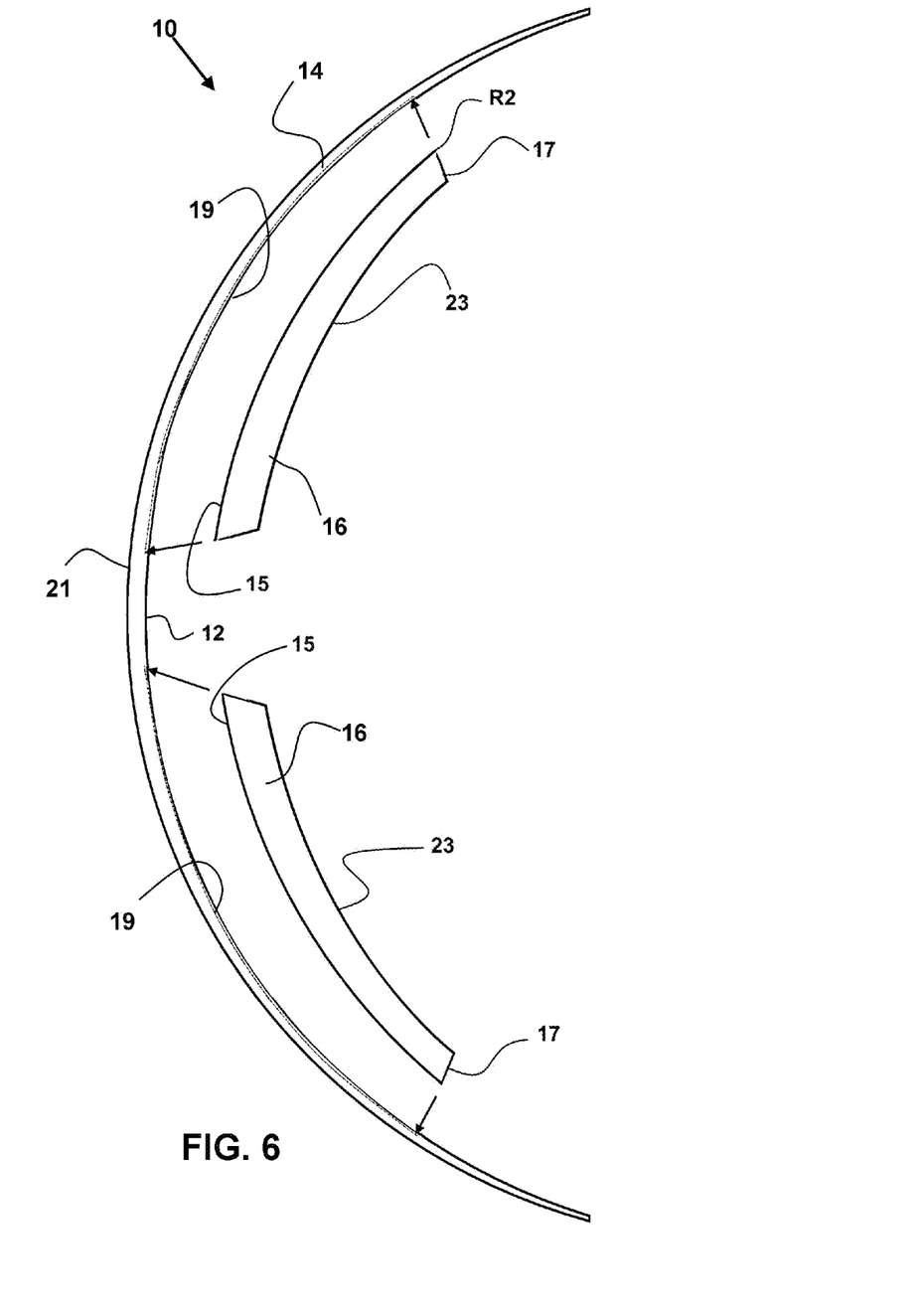
FIG. 6 shows a similar configuration to FIG. 5, but where recesses are formed into the curved surface of the first lens portion matching the perimeter shape of the projecting portions, to help register the projecting portions in position prior to adhesion or sonic welding or other permanent attachment to the first lens portion.

In FIG. 6 is shown a similar configuration to that of FIG. 5, but where recesses 19 depend into the curved first surface 12 of the first lens portion 14. The perimeter of the recesses 19 are formed to a shape matching the perimeter defined by the sidewall 17 of the projecting portions 16. This recess 19 even if only a few thousandths of an inch in depth provides a means to register the projecting portions 16, in position against the first surface 12 of the first lens portion 14, prior to adhesion or sonic welding 26 or other permanent attachment to the first lens portion 14.

Figure 7:
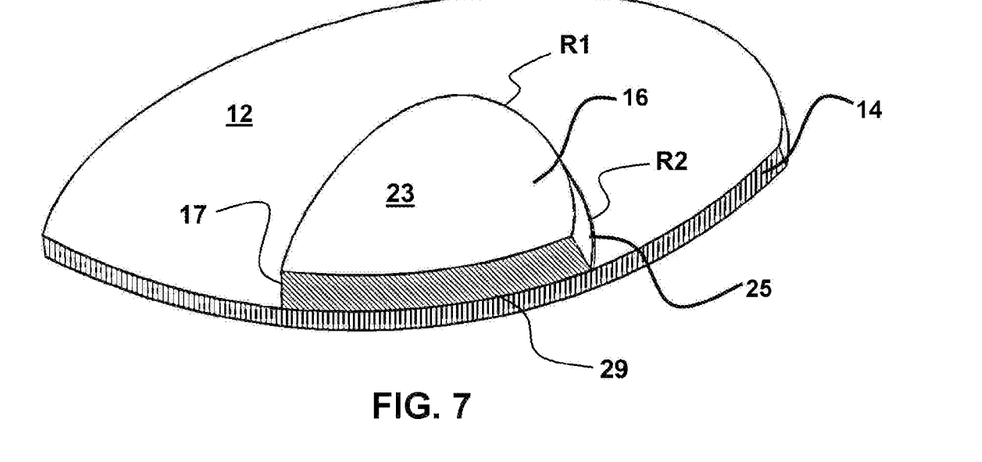
FIG. 7 is a sectional view through a welded or adhered projecting portion separated by a micronic gap from the first surface of the first lens portion as in FIG. 5.

FIG. 7 is an example of sectional view through an affixed projecting portion 16 adjacent the first surface 12 of a surrounding first lens portion 14, such as in FIG. 5. While too small to depict, a micro cavity or gap 19 is formed between the mating surface 15 of the projecting portion 16 and the first surface 12 of the first lens portion 14. It is important that a hermetic seal be formed by the welding or adhesive used for engagement to seal this from exterior air and particulate. Also depicted is the curve or radius R2 at the intersection 25 of the sidewall 17 and first surface 12. A similar curve or radius R1 is formed at the transition of the sidewall 17 to the first side 23 of the projecting portion 16. Such as noted can be formed during a laser or sonic weld, or formed into the perimeter edges of the sidewall 17 of the projecting portion 16 prior to the engagement.

Figure 8:
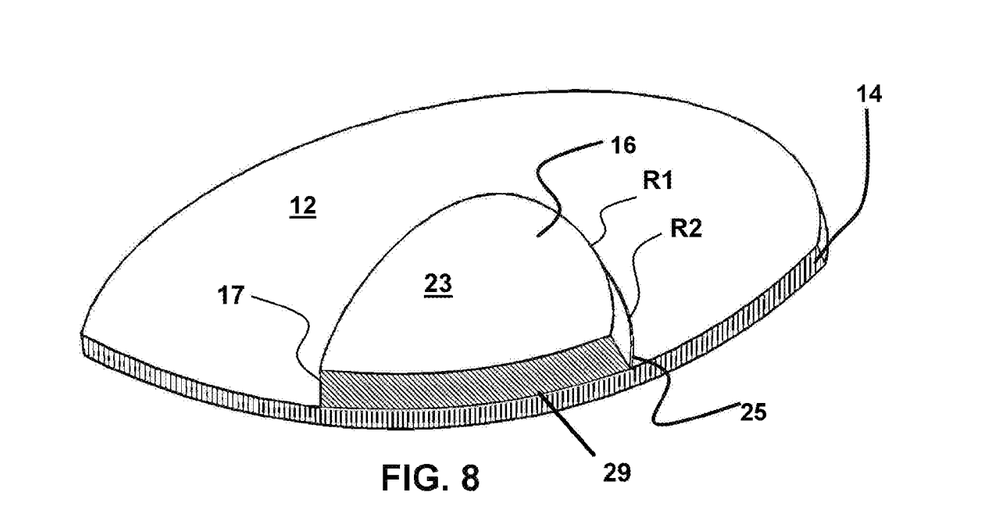
FIG. 8 shows a sectional view through a sonically welded or adhered projecting portion to a surrounding first lens portion having a recess therein as in FIG. 6.

FIG. 8 shows a sectional view similar to that of FIG. 7, but where a recess 19 shaped to match the perimeter shape of the projecting portion 16, depends into the first surface 12 of the first lens portion 14. A sonic weld 25 is shown to form the permanent engagement and formed structure of projecting portion 16 with the first lens portion 14, although an adhesive may also be employed.

Figure 9:
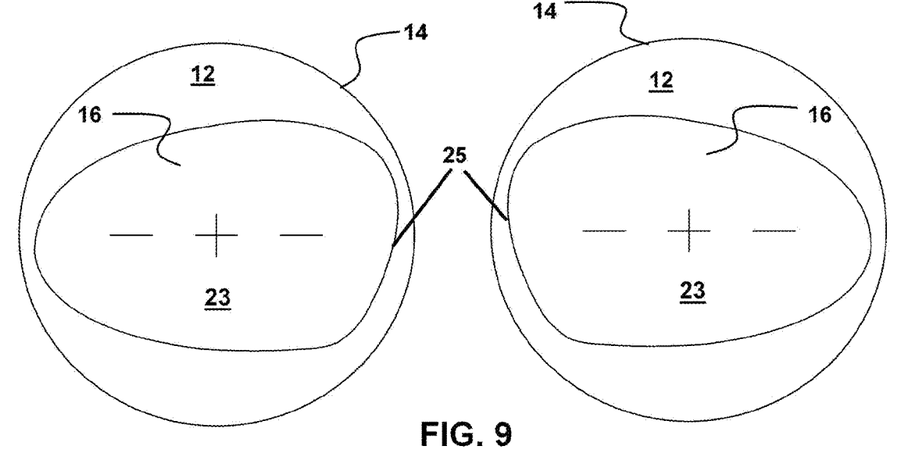
FIGS. 9 and 10 show projecting portions extending from first lens portions which are configured for engagement to conventional eyeglass frames using the perimeter edge of the first lens portions.
Figure 10:
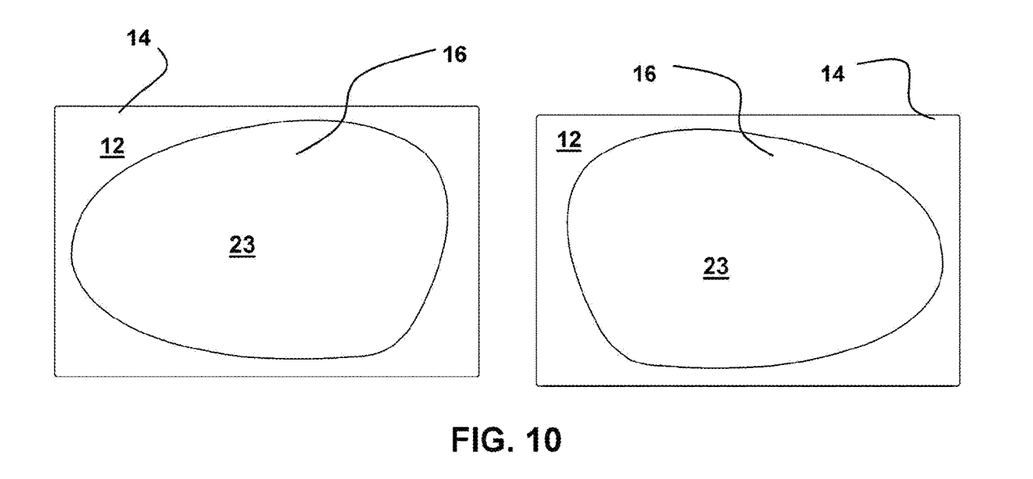

FIGS. 9 and 10 show projecting portions 16 extending from surrounding first lens portions 14, which are configured for engagement to conventional eyeglass frames using the perimeter edge of the first lens portions 14 which is much thinner than the formed structure of the projecting portion 16 and engaged first lens portion 14 at the perimeter edge of the projecting portion 16.

Figures 11, 12:
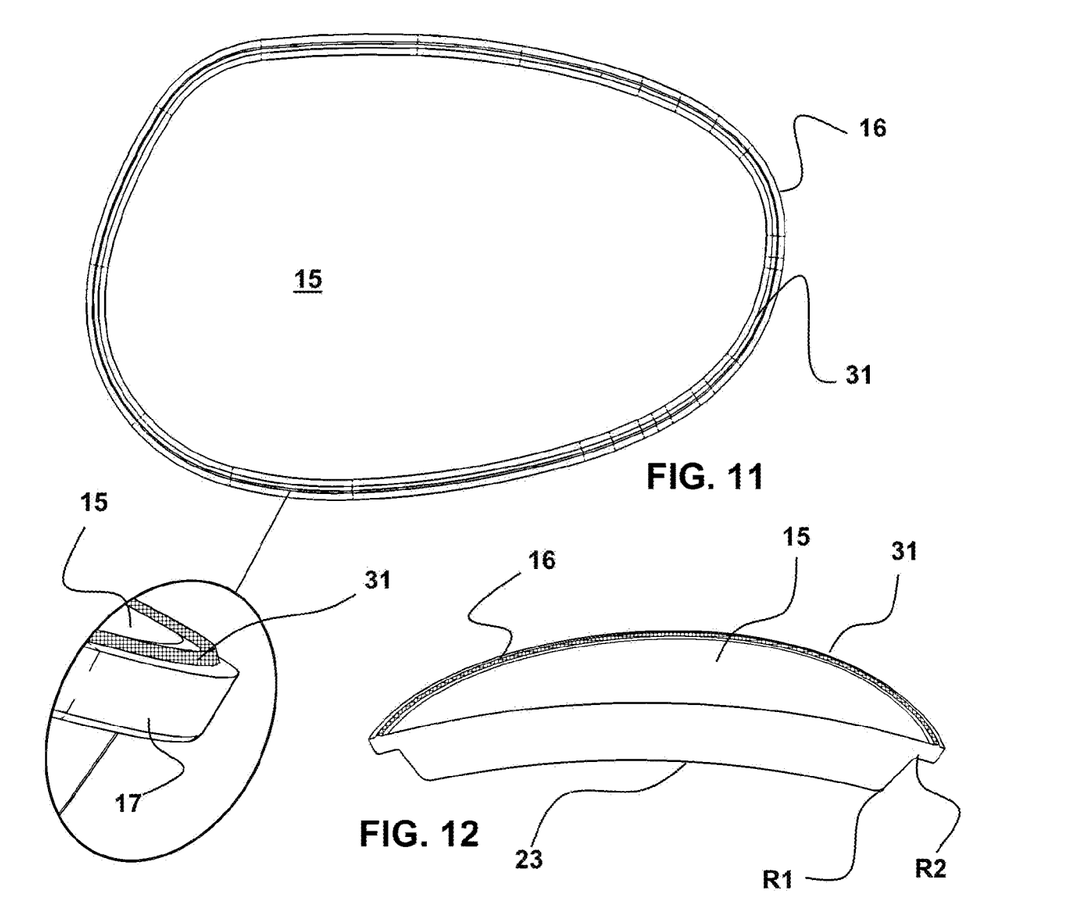
FIG. 11 shows a preformed projecting portion having a curved mating surface which is identical to the curve of the first surface of a first lens component to which it mates, and showing a pointed or triangular projection running around the perimeter of the mating surface.
FIG. 12 shows a sectional view of the projecting portion of FIG. 11 showing the triangular projection an a ledge defining the perimeter edge of the projecting portion.

In FIG. 11 is shown a preformed projecting portion 16 having a curved mating surface 15 which has a base curve identical to the curve of the first surface 12 of a first lens component 14 to which it mates. Also shown is a ridge 31 having a generally triangular shape, which extends around the perimeter of the mating surface 15, and will form a hermetic seal around the micro cavity 29 when engaged into the first lens portion 14 by sonic welding. It has been found that forming this ridge 31 in this triangular shape, causes it to pierce and become welded into the material of the first lens component 14 by the vibration transmitted from a sonic welder. This forms a permanent fused engagement and a hermetic seal around the micro cavity 29.

Shown in FIG. 12 is a sectional view of the projecting portion 16 of FIG. 11. Also shown is the triangular ridge 31 projecting around the perimeter edge of the mating surface 15 of the projecting portion 16.

Figure 13:
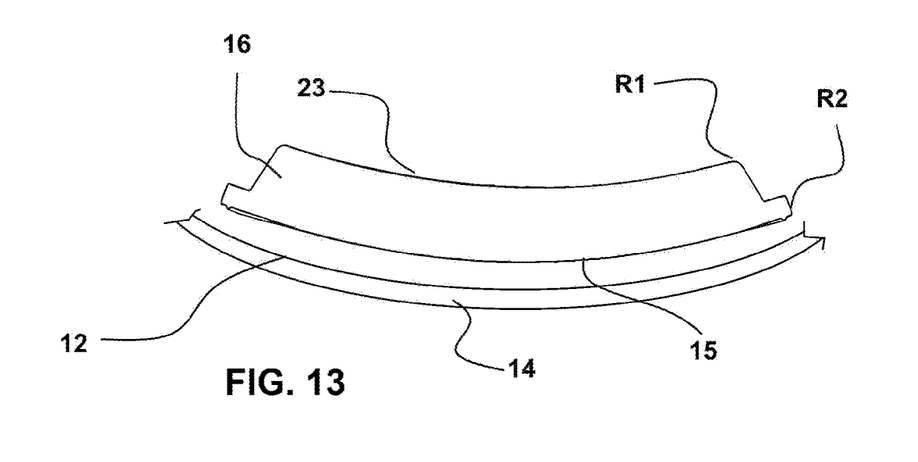
FIG. 13 shows the base curve of the mating surface of the projecting portion, matching the base curve of the first surface of the first lens component.

In FIG. 13 is shown that the base curve of the mating surface 15 of the projecting portion 16, matches the base curve of the first surface 12 of the first lens component 14.

Figure 14:
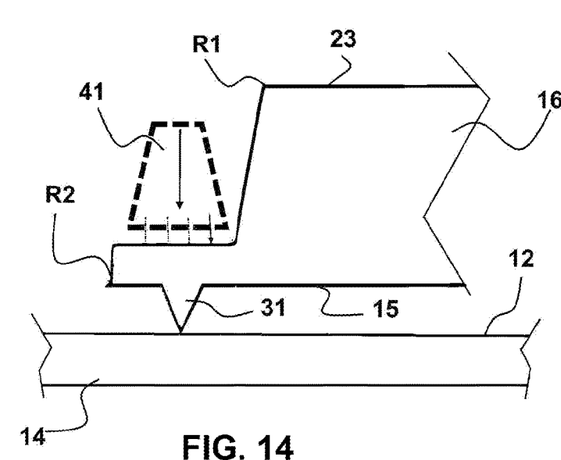
FIG. 14 depicts a mode of engaging a preformed projecting portion with the first surface of the first lens portion using a sonic welder which drives the triangular connector into the material forming the first lens member and fuses it therewith to form a hermetic seal.
Figure 15:
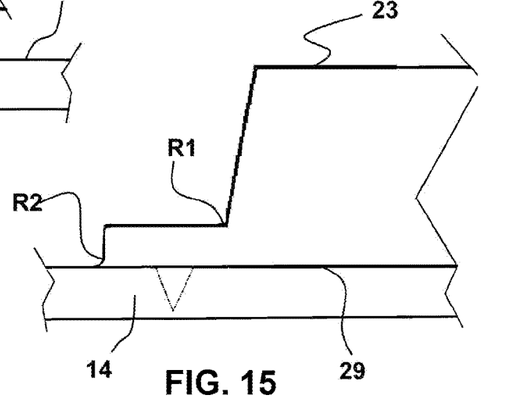
FIG. 15 shows the sealed engagement of the projecting member of FIG. 14 to the first lens portion.

In FIG. 14 is an example of engaging a preformed projecting portion 16 against the first surface 12 of the first lens portion 14 using a sonic welder 41 which drives the triangular ridge 31 into a fused engagement with the optic material forming the first lens member 14 and fuses it therewith to form a hermetic seal around the formed micro cavity 29. Shown in FIG. 15 is the resulting hermetically sealed engagement of the projecting ridge 31 shown in FIG. 14 in a fused engagement into the first lens portion 14.

Figures 16, 17:
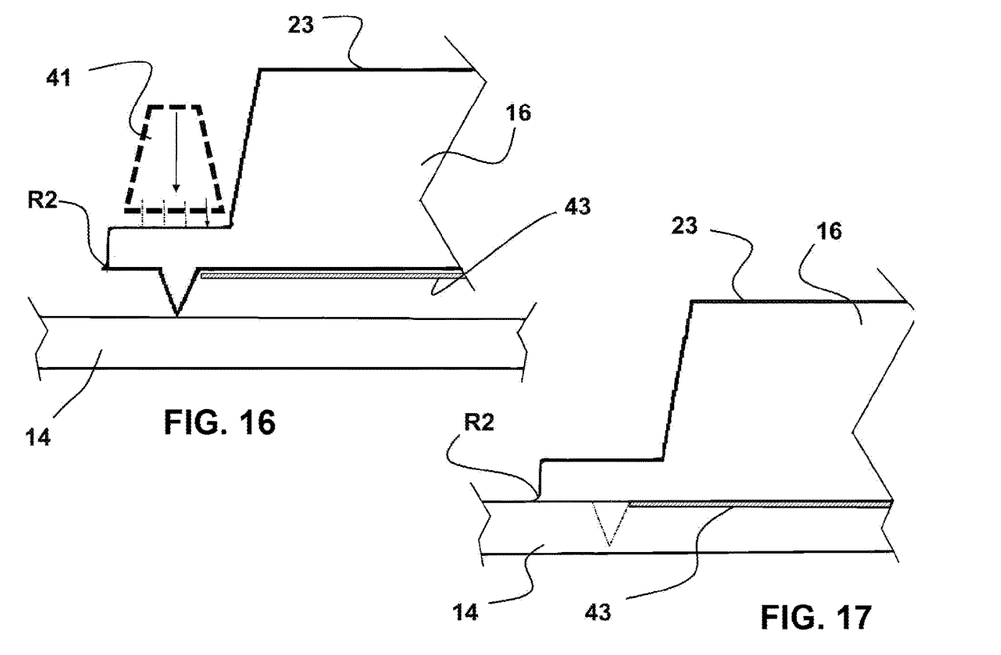
FIG. 16 depicts the sonic welder used to join a projecting member to a first lens portion, where filtering media is included only in or on the projecting portion.
FIG. 17 depicts the projecting portion of FIG. 16 engaged by the fused triangular ridge into the material forming the first lens portion

FIG. 16 depicts the sonic welder 41 used to join a projecting portion 16 against and to a first lens portion 14. As shown, light filtering medium, such as one or a combination of light filtering medium from a group including reflective film, a polarizing film or layer, an arc flash stopping layer, a Photo Chromatic layer or film, colorized optical, is included into the formed projecting portion 16. The pre formed projecting portion 16 can then be affixed to the chosen first lens portion 14 to form the component device.

FIG. 17 depicts the projecting portion 16 in FIG. 16 engaged to the first lens portion 14, by the fused triangular ridge 31 which is fused into the material forming the first lens portion 14 by the action of the sonic welder 41. As shown, only the projecting portion 16 has light filtering medium 43, however as noted, since the two components are formed separately and joined, the first lens portion 14 might also have one or a combination of light medium from the group included therein.

Figures 18, 19:
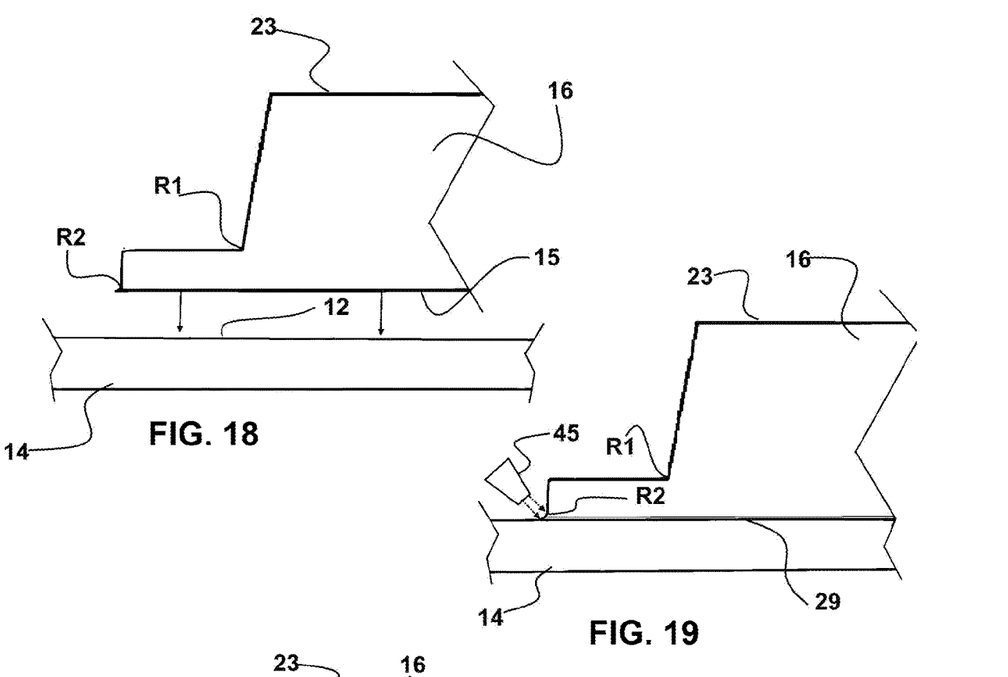
FIGS. 18 and 19 show the engagement of the projecting portion with the first lens portion by laser welding around the perimeter edge which is formed as a radius or curve.

FIGS. 18 and 19 show the engagement of the projecting portion 16 with the first lens portion 14 by laser welding 45 around the perimeter edge of the projecting portion 16 which as noted should be formed as a radius R2 or curve.

Figures 20, 21:
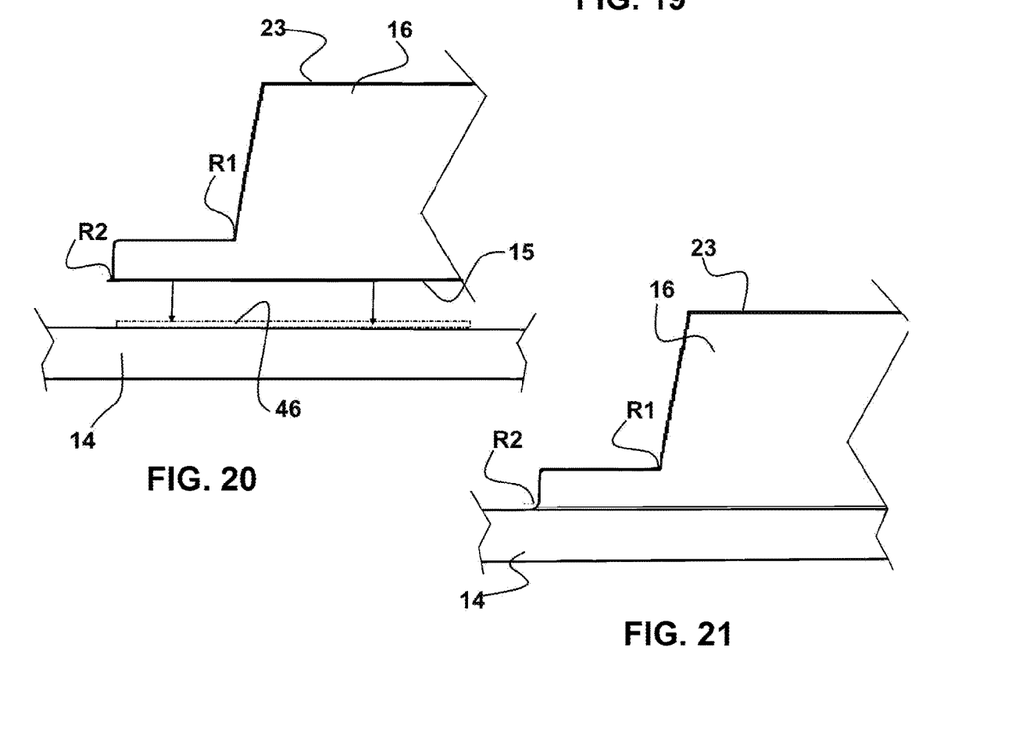
FIGS. 20 and 21 depict the joining of the mating surface of the projecting portion adjacent the first surface of the first lens portion using an optically correct adhesive such as sold by 3M company.

FIGS. 20 and 21 depict the joining of the mating surface 15 of the projecting portion 16 adjacent the first surface 12 of the first lens portion 14 using an optically correct adhesive 46 such as sold by 3M company. This hermetically seals the micro cavity 29 formed between the two surfaces as noted is desired to prevent optical quality issues from moisture and micro particles.

As noted above, in a method of formation of the lens herein, a first lens portion 14 would be formed with a perimeter adapted for engagement to eyewear frames. Projecting portions 16 would be formed with the desire radius R1 and R2, and in a shape defined by the sidewall 17 adapted to form a prescription lens required. Next the mating surface 15 of the projecting portion 16 would be engaged to the first surface 12 of the first lens portion 14 using sonic welding, laser, or adhesive, or the like. Optional steps can include positioning one or a plurality of filter medium 43 into the formed projecting portion 16, and, grinding the first side 23 of the raised portion 16, prior to engagement to the first lens portion 14, and forming recesses in the first surface 12 of the first lens portion 14, which provide registration points for the projecting portions 16 to be engaged.

While all of the fundamental characteristics and features of the lens system herein have been shown and described herein, with reference to particular embodiments thereof, a latitude of modification, various changes and substitutions are intended in the foregoing disclosure and it will be apparent that in some instances, some features or steps in the invention may be employed without a corresponding use of other features or steps without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A corrective lens comprising:
a first lens portion extending in a panoramic curve from a first end to a second end thereof;
said first lens portion having a first surface having a first curve opposite a second surface having a second curve;
a first projecting portion having a first sidewall defining a perimeter thereof;
said first projecting portion having a first side thereof opposite a mating surface thereof;
said first side of said first projecting portion being formable to configure said first projecting portion to a first corrective lens;
a second projecting portion having a second sidewall defining a perimeter thereof;
said second projecting portion having a first side thereof opposite a mating surface thereof;
said first side of said second projecting portion being formable to configure said second projecting portion to a second corrective lens;
said first projecting portion in a permanent connection thereof to said first surface of said first lens potion;
said second projecting portion in a permanent connection thereof to said first surface of said first lens potion;
said first lens portion configured for an operative engagement with an eyeglass frame or goggle which is positionable upon a user to locate the first projecting portion aligned with a first eye of the user and the second projecting portion aligned with a second eye of the user and positioning the curved first lens portion as a curved shield in front of both eyes of the user.

2. The corrective lens of claim 1 additionally comprising:
a base curve of both said mating surface of said first projection and said mating surface of said second projection being substantially equal to a base curve of said first surface of said first lens portion.

3. The corrective lens of claim 2 additionally comprising:
said corrective lens having a shadowless appearance, in a viewing thereof from the second surface of said first lens portion.

4. The corrective lens of claim 3 additionally comprising:
said first projecting portion extending from a first side of said first sidewall thereof positioned at a central area of said first lens portion in-between said first end and second end of said first lens portion, to a second side of said first sidewall thereof located adjacent said first end of said first lens portion;
said second projecting portion extending from a first side of said second sidewall at said central area of said first lens portion, to a second side of said second sidewall thereof located adjacent said second end of said first lens portion;
said first side of said first projecting portion being formable to configure said first corrective lens having one or both of, a panoramic progressive vision correction between said first side of said sidewall and said second side of said sidewall of said first projecting portion, and a vertical progressive vision correction thereof, between a top of said first sidewall of said first projecting portion and an opposite bottom of said first sidewall of said first projecting portion; and
said first side of said second projecting portion being formable to configure said second corrective lens with one or both of, a panoramic progressive vision correction thereof between said first side of said second sidewall thereof and said second side of said second sidewall thereof, and a vertical progressive vision correction thereof, between a top of said second sidewall of said second projecting portion and an opposite bottom of said second sidewall of said second projecting portion.

5. The corrective lens of claim 4 additionally comprising:
said first projecting portion having a first recess formed into said first sidewall thereof, said first recess extending from said first side of said first sidewall thereof to said bottom of said first sidewall thereof;
said second projecting portion having a second recess formed into said second sidewall thereof, said second recess extending from said first side of said second sidewall thereof to said bottom of said second sidewall thereof; and
said first recess positioned on an opposite side of said central area of said first lens portion from said second recess.

6. The corrective lens of claim 2 additionally comprising:
said first projecting portion extending from a first side of said first sidewall thereof positioned at a central area of said first lens portion in-between said first end and second end of said first lens portion, to a second side of said first sidewall thereof located adjacent said first end of said first lens portion;
said second projecting portion extending from a first side of said second sidewall at said central area of said first lens portion, to a second side of said second sidewall thereof located adjacent said second end of said first lens portion;
said first side of said first projecting portion being formable to configure said first corrective lens having one or both of, a panoramic progressive vision correction between said first side of said sidewall and said second side of said sidewall of said first projecting portion, and a vertical progressive vision correction thereof, between a top of said first sidewall of said first projecting portion and an opposite bottom of said first sidewall of said first projecting portion; and
said first side of said second projecting portion being formable to configure said second corrective lens with one or both of, a panoramic progressive vision correction thereof between said first side of said second sidewall thereof and said second side of said second sidewall thereof, and a vertical progressive vision correction thereof, between a top of said second sidewall of said second projecting portion and an opposite bottom of said second sidewall of said second projecting portion.

7. The corrective lens of claim 6 additionally comprising:
said first projecting portion having a first recess formed into said first sidewall thereof, said first recess extending from said first side of said first sidewall thereof to said bottom of said first sidewall thereof;
said second projecting portion having a second recess formed into said second sidewall thereof, said second recess extending from said first side of said second sidewall thereof to said bottom of said second sidewall thereof; and said first recess positioned on an opposite side of said central area of said first lens portion from said second recess.

8. The corrective lens of claim 2 additionally comprising:
said first lens portion having one or a combination of light filtering medium, from a group of light medium including, reflective film, a polarizing film or layer, an arc flash stopping layer, a photo chromatic layer or film, and colorized optical material.

9. The corrective lens of claim 1 additionally comprising:
said corrective lens having a shadowless appearance, in a viewing thereof from the second surface of said first lens portion.

10. The corrective lens of claim 9 additionally comprising:
said first projecting portion extending from a first side of said first sidewall thereof positioned at a central area of said first lens portion in-between said first end and second end of said first lens portion, to a second side of said first sidewall thereof located adjacent said first end of said first lens portion;
said second projecting portion extending from a first side of said second sidewall at said central area of said first lens portion, to a second side of said second sidewall thereof located adjacent said second end of said first lens portion;
said first side of said first projecting portion being formable to configure said first corrective lens having one or both of, a panoramic progressive vision correction between said first side of said sidewall and said second side of said sidewall of said first projecting portion, and a vertical progressive vision correction thereof, between a top of said first sidewall of said first projecting portion and an opposite bottom of said first sidewall of said first projecting portion; and
said first side of said second projecting portion being formable to configure said second corrective lens with one or both of, a panoramic progressive vision correction thereof between said first side of said second sidewall thereof and said second side of said second sidewall thereof, and a vertical progressive vision correction thereof, between a top of said second sidewall of said second projecting portion and an opposite bottom of said second sidewall of said second projecting portion.

11. The corrective lens of claim 10 additionally comprising:
said first projecting portion having a first recess formed into said first sidewall thereof, said first recess extending from said first side of said first sidewall thereof to said bottom of said first sidewall thereof;
said second projecting portion having a second recess formed into said second sidewall thereof, said second recess extending from said first side of said second sidewall thereof to said bottom of said second sidewall thereof; and
said first recess positioned on an opposite side of said central area of said first lens portion from said second recess.

12. The corrective lens of claim 11 additionally comprising:
said first projecting portion having one or a combination of light filtering medium, from a group of light medium including, reflective film, a polarizing film or layer, an arc flash stopping layer, a photo chromatic layer or film, and colorized optical material.

13. The corrective lens of claim 10 additionally comprising:
said first projecting portion having one or a combination of light filtering medium, from a group of light medium including, reflective film, a polarizing film or layer, an arc flash stopping layer, a photo chromatic layer or film, and colorized optical material.

14. The corrective lens of claim 9 additionally comprising:
said first lens portion having one or a combination of light filtering medium, from a group of light medium including, reflective film, a polarizing film or layer, an arc flash stopping layer, a photo chromatic layer or film, and colorized optical material.

15. The corrective lens of claim 1 additionally comprising:
said first projecting portion extending from a first side of said first sidewall thereof positioned at a central area of said first lens portion in-between said first end and second end of said first lens portion, to a second side of said first sidewall thereof located adjacent said first end of said first lens portion;
said second projecting portion extending from a first side of said second sidewall at said central area of said first lens portion, to a second side of said second sidewall thereof located adjacent said second end of said first lens portion;
said first side of said first projecting portion being formable to configure said first corrective lens having one or both of, a panoramic progressive vision correction between said first side of said sidewall and said second side of said sidewall of said first projecting portion, and a vertical progressive vision correction thereof, between a top of said first sidewall of said first projecting portion and an opposite bottom of said first sidewall of said first projecting portion; and
said first side of said second projecting portion being formable to configure said second corrective lens with one or both of, a panoramic progressive vision correction thereof between said first side of said second sidewall thereof and said second side of said second sidewall thereof, and a vertical progressive vision correction thereof, between a top of said second sidewall of said second projecting portion and an opposite bottom of said second sidewall of said second projecting portion.

16. The corrective lens of claim 15 additionally comprising:
said first projecting portion having a first recess formed into said first sidewall thereof, said first recess extending from said first side of said first sidewall thereof to said bottom of said first sidewall thereof;
said second projecting portion having a second recess formed into said second sidewall thereof, said second recess extending from said first side of said second sidewall thereof to said bottom of said second sidewall thereof; and
said first recess positioned on an opposite side of said central area of said first lens portion from said second recess.

17. The corrective lens of claim 1 additionally comprising:
said first lens portion having one or a combination of light filtering medium, from a group of light medium including, reflective film, a polarizing film or layer, an arc flash stopping layer, a photo chromatic layer or film, and colorized optical material.

18. The corrective lens of claim 1 additionally comprising:
- said first lens portion having one or a combination of light filtering medium, from a group of light medium including, reflective film, a polarizing film or layer, an arc flash stopping layer, a photo chromatic layer or film, and colorized optical material.

19. The corrective lens of claim 1 additionally comprising:
- said first projecting portion having one or a combination of light filtering medium, from a group of light medium including, reflective film, a polarizing film or layer, an arc flash stopping layer, a photo chromatic layer or film, and colorized optical material, and
- said second projecting portion having one or a combination of light filtering medium, from a group of light medium including, reflective film, a polarizing film or layer, an arc flash stopping layer, a photo chromatic layer or film, and colorized optical material.

* * * * *